United States Patent [19]

Kanno et al.

[11] Patent Number: 5,726,128

[45] Date of Patent: Mar. 10, 1998

[54] BENZYLOXYPYRIMIDINE DERIVATIVE, PROCESSES FOR PRODUCING THE SAME AND HERBICIDAL COMPOSITION

[75] Inventors: Hisashi Kanno; Yoshikazu Kubota; Tsutomu Sato; Masato Arahira, all of Iwaki, Japan

[73] Assignee: Kureha Kagaku Kogyo Kabushiki Kaisha, Japan

[21] Appl. No.: 525,059

[22] Filed: Sep. 8, 1995

[30] Foreign Application Priority Data

Sep. 14, 1994 [JP] Japan .................. 6-247058

[51] Int. Cl.$^6$ .................. A01N 43/54; C07D 239/46; C07D 239/60

[52] U.S. Cl. .................. 504/243; 544/299; 544/302; 544/303; 544/312; 544/313; 544/314; 544/309

[58] Field of Search .................. 544/299, 302, 544/303, 312, 313, 314, 309; 504/243

[56] References Cited

U.S. PATENT DOCUMENTS

| | | | |
|---|---|---|---|
| 4,770,691 | 9/1988 | Nezu et al. | 71/92 |
| 4,985,066 | 1/1991 | Wada et al. | 71/92 |
| 5,599,770 | 2/1997 | Kubota et al. | 504/243 |
| 5,616,537 | 4/1997 | Yokota et al. | 504/243 |

FOREIGN PATENT DOCUMENTS

| | | |
|---|---|---|
| 27 34 827 | 2/1978 | Germany . |
| 2 285 045 | 5/1995 | United Kingdom . |

OTHER PUBLICATIONS

J. Chem. Soc., 1959, pp. 525–530.
J. C. S. Perkin I, 1975, pp. 1798–1802.
Agr. Biol. Chem., 30, 1966, pp. 896–905.
J. Chem. Soc., 1965, pp. 5542–5551.
Niedermann et al., Chemical Abstracts, vol. 123, entry 340190 (1995).

*Primary Examiner*—John M. Ford
*Attorney, Agent, or Firm*—Parkhurst & Wendel, L.L.P

[57] ABSTRACT

1. A benzyloxypyrimidine derivative of the formula (I):

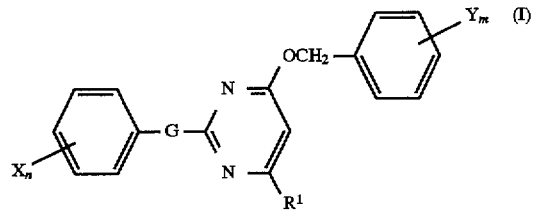

wherein $R^1$ represents hydrogen, a halogen, $C_1$–$C_4$ alkyl, $C_1$–$C_4$ haloalkyl, $C_1$–$C_4$ alkoxy, $C_1$–$C_4$ haloalkoxy, $C_3$–$C_5$ alkenyloxy, $C_1$–$C_4$ alkylthio, or cyano;

each X, which may be identical or different if n is greater than 1, represents a halogen, $C_1$–$C_4$ alkyl, $C_1$–$C_4$ haloalkyl, $C_1$–$C_4$ alkoxy, $C_1$–$C_4$ haloalkoxy, or $C_1$–$C_4$ haloalkyl;

each Y, which may be identical or different if m is greater than 1, represents a halogen, $C_1$–$C_4$ alkyl, $C_1$–$C_4$ haloalkyl, $C_1$–$C_4$ alkoxy, or $C_1$–$C_4$ haloalkoxy;

G represents O or S; and n and m each independently represent an integer of 0 to 5.

8 Claims, No Drawings

BENZYLOXYPYRIMIDINE DERIVATIVE, PROCESSES FOR PRODUCING THE SAME AND HERBICIDAL COMPOSITION

BACKGROUND OF THE INVENTION

The present invention relates to a benzyloxypyrimidine derivative, processes for producing the derivative and a herbicidal composition containing the derivative as an active ingredient.

it has been demanded a herbicide having superior herbicidal activity, such as a reliable herbicidal effect at such a low application dose that the residual amount in the environment advantageously decreases, good selectivity between crops and weeds regardless of environmental condition changes and low phytotoxicity to the succeeding crop cultivated in a double cropping system.

The present invention was achieved for the purpose of meeting the existing demands as set forth above.

The object of the present invention is, therefore, to provide a novel compound having an excellent herbicidal activity, processes for producing the derivative and a herbicidal composition containing such compound as an active ingredient.

The present inventors, with a view to discover a novel industrially useful benzyloxypyrimidine derivative, have conducted extensive researches and have found that a specific benzyloxypyrimidine derivative has a high herbicidal activity. Based on the finding, the present invention has been accomplished.

SUMMARY OF THE INVENTION

In a first aspect of the present invention, it is provided a benzyloxypyrimidine derivative of the formula (I):

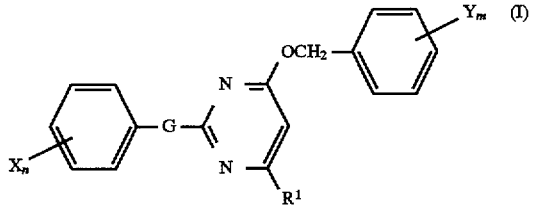

wherein $R^1$ represents hydrogen, a halogen, $C_1$–$C_4$ alkyl, $C_1$–$C_4$ haloalkyl, $C_1$–$C_4$ alkoxy, $C_1$–$C_4$ haloalkoxy, $C_3$–$C_5$ alkenyloxy, $C_1$–$C_4$ alkylthio, or cyano;

each X, which may be identical or different if n is greater than 1, represents a halogen, $C_1$–$C_4$ alkyl, $C_1$–$C_4$ haloalkyl, $C_1$–$C_4$ alkoxy, $C_1$–$C_4$ haloalkoxy, or $C_1$–$C_4$ haloalkylthio;

each Y, which may be identical or different if m is greater than 1, represents a halogen, $C_1$–$C_4$ alkyl, $C_1$–$C_4$ haloalkyl, $C_1$–$C_4$ alkoxy, or $C_1$–$C_4$ haloalkoxy;

G represents O or S; and n and m each independently represent an integer of 0 to 5.

In a second aspect of the present invention, it is provided a process for producing a benzyloxypyrimidine derivative of the formula (I):

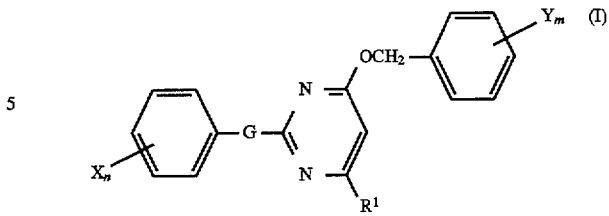

wherein $R^1$, X, Y, G, m, and n are as defined above, which comprises reacting a 2-(leaving-group-substituted) pyrimidine derivative of the formula (II):

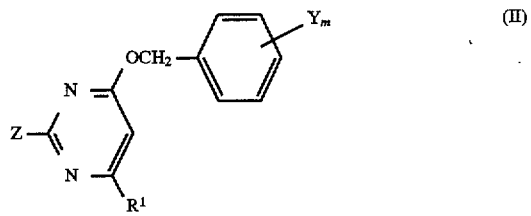

wherein $R^1$, Y, and m are as defined in claim 1; and Z represents a halogen, $C_1$–$C_4$ alkylsulfonyl, $C_7$–$C_9$ aralkylsulfonyl, or arylsulfonyl, with a phenol or thiophenol compound of the formula (III):

wherein X, G, and n are as defined above.

In a third aspect of the present invention, it is provided a process for producing of a benzyloxypyrimidine derivative of the formula (I):

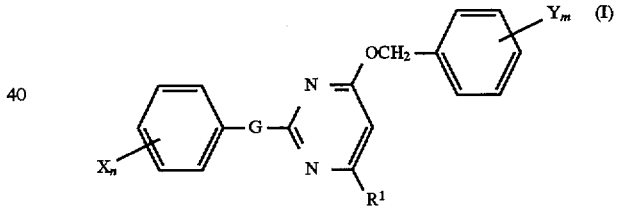

wherein $R^1$, X, Y, G, m, and n are as defined above, which comprises reacting a phenoxy or phenylthio pyrimidine compound of the formula (IV):

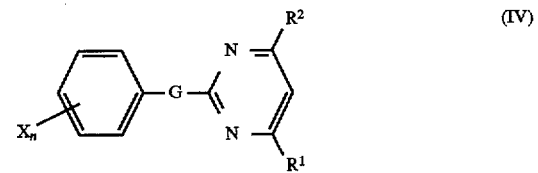

wherein $R^1$, X, G, and n are as defined above; and $R^2$ represents a halogen, with a benzyl alcohol compound of the formula (V):

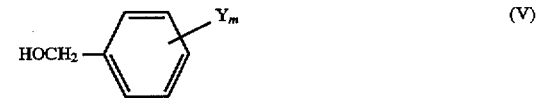

wherein Y and m are as defined above.

In a fourth aspect of the present invention, it is provided a herbicidal composition comprising a herbicidally effective amount of a benzyloxypyrimidine derivative of the formula (I):

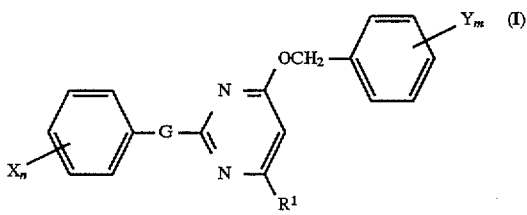

wherein $R^1$, X, Y, G, m, and n are as defined above, and an adjuvant.

DETAILED DESCRIPTION OF THE INVENTION

Atomic symbols, abbreviations, or rational formulae given in parentheses after the description of atoms and substituents set forth below are employed in the tables 1, 2 and 3 showing examples of the compounds.

$R^1$ includes the following atoms and substituents:

hydrogen (H);

a halogen such as fluorine (F), chlorine (Cl), bromine (Br), and iodine (I);

$C_1$–$C_4$ alkyl such as methyl (Me), ethyl, 1-methylethyl, 1,1-dimethylethyl, propyl, and butyl;

$C_1$–$C_4$ haloalkyl such as trifluoromethyl ($CF_3$), fluoromethyl, difluoromethyl, and 2,2,2-trifluoroethyl;

$C_1$–$C_4$ alkoxy such as methoxy (OMe), ethoxy (OEt), (1-methylethyl)oxy, propoxy, (2-methylpropyl)oxy, (1-methylpropyl)oxy, and butoxy;

$C_1$–$C_4$ haloalkoxy such as difluoromethoxy, 1,1,2,2-tetrafluoroethoxy, 2,2,2-trifluoroethoxy, 2-fluoroethoxy, 2-bromo-1,1,2-trifluoroethoxy, 2,2,3,3,3-pentafluoropropoxy, 1,1,2,3,3,3-hexafluoropropoxy, and 2-chloro-1,1,2-trifluoroethoxy;

$C_3$–$C_5$ alkenyloxy such as (2-propenyl)oxy ($OCH_2CH=CH_2$), (2-methyl-2-propenyl)oxy, crotyloxy, (3-methyl-2-butenyl)oxy ($OCH_2CH=CMe_2$), and (3-methyl-3-butenyl)oxy;

$C_1$–$C_4$ alkylthio such as methylthio (SMe) and ethylthio (SEt); and cyano (CN).

Preferably, $R^1$ represents hydrogen, a halogen, methyl, methoxy, ethoxy, methylthio, ethylthio, or cyano.

Each X includes the following atoms and groups:

a halogen such as fluorine (F), chlorine (Cl), bromine (Br), and iodine (I);

$C_1$–$C_4$ alkyl such as methyl (Me), ethyl, 1-methylethyl, and butyl;

$C_1$–$C_4$ haloalkyl such as trifluoromethyl ($CF_3$), fluoromethyl, difluoromethyl and 2,2,2-trifluoroethyl;

$C_1$–$C_4$ alkoxy such as methoxy, ethoxy, (1-methylethyl)oxy, and (1-methylpropyl)oxy;

$C_1$–$C_4$ haloalkoxy such as difluoromethoxy, trifluoromethoxy ($OCF_3$), 1,1,2,2-tetrafluoroethoxy, 2,2,2-trifluoroethoxy ($OCH_2CF_3$), 2-fluoroethoxy, 2-bromo-1,1,2-trifluoroethoxy, 2,2,3,3,3-pentafluoropropoxy ($OCH_2CF_2CF_3$), 1,1,2,3,3,3-hexafluoropropoxy, and 2-chloro-1,1,2-trifluoroethoxy; and $C_1$–$C_4$ haloalkylthio such as trifluoromethylthio ($SCF_3$), difluoromethylthio, and 2,2,2-trifluoroethylthio.

Preferably, X is not present (i.e. n=0) or each X represents a halogen (more preferably chlorine), trifluoromethyl, 2,2,2-trifluoroethoxy, or 2,2,3,3,3-pentafluoropropoxy.

More preferably, X is not present (i.e. n=0) or each X represents a halogen (more preferably chlorine), trifluoromethyl, 2,2,2-trifluoroethoxy, or 2,2,3,3,3-pentafluoropropoxy which is bonded to the position 3.

Each Y includes the following atoms and groups:

a halogen such as fluorine, chlorine (Cl), bromine, and iodine;

$C_1$–$C_4$ alkyl such as methyl (Me), ethyl, 1-methylethyl, and butyl;

$C_1$–$C_4$ haloalkyl such as trifluoromethyl ($CF_3$), fluoromethyl, difluoromethyl, and 2,2,2-trifluoroethyl; and $C_1$–$C_4$ alkoxy such as methoxy (OMe), ethoxy, (1-methylethyl)oxy, and (1-methylpropyl)oxy.

Preferably, Y is not present (i.e. m=0) or each Y represents a halogen (more preferably chlorine), methyl, methoxy, or trifluoromethyl.

More preferably, Y is not present (i.e. m=0) or each Y represents a halogen (still preferably chlorine), methyl, methoxy, or trifluoromethyl which is bonded to the position 3 and/or 4.

Preferably, m represents an integer of 0 to 3, more preferably 0 or 1.

Preferably, n represents an integer of 0 to 3, more preferably 0, 1 or 2.

When m and n are more than 1, X and Y may be identical or different each other, respectively.

More preferably, the compounds of the above formula (I) contain the combination of the preferred substituents $R^1$, X and Y selected from the following.

$R^1$ represent hydrogen, a halogen, methyl, methoxy, ethoxy, methylthio, ethylthio, or cyano.

X is not present (i.e. n=0) or represents a halogen (still preferably chlorine), trifluoromethyl, 2,2,2-trifluoroethoxy, or 2,2,3,3,3-pentafluoropropoxy which is bonded to the position 3.

Y is not present (i.e. m=0) or represents a halogen (still preferably chlorine), methyl, or trifluoromethyl which is bonded to the position 3 and/or 4.

Z includes the following atoms and groups:

$C_1$–$C_4$ alkylsulfonyl such as methylsulfonyl ($MeSO_2$) and ethylsulfonyl; and $C_7$–$C_9$ aralkylsulfonyl such as benzylsulfonyl; and arylsulfonyl (generally $C_6$–$C_8$) such as phenylsulfonyl and 4-methylphenylsulfonyl.

In the Tables 1, 2 and 3, $R^1$, $R^2$, $R^3$, X, and Y are each represented as below.

Methyl and ethyl are represented by Me and Et, respectively.

The bonded positions of X and Y on the benzene ring are each represented by a figure followed by a hyphen symbol (–) which precedes the substituent X or Y. For example, 3-$CF_3$ means a trifluoromethyl group bonded to the position 3 (meta position). Similarly, 3-$OCH_2CF_2CF_3$ means a 2,2,3,3,3-pentafluoropropoxy group bonded to the position 3 (meta position).

The numbers (m and n) of atoms and substituents bonded to the benzene ring are indicated by an unsubscript figure (meaning the same size) after the atoms and substituents. When this figure is likely to be confused with the number of atoms constituting a substituent, the substituent may be parenthesized and the number thereof may be indicated after the parenthesis. For example, 2,3,4,5,6-F5 means that a total of five fluorine atoms are bonded to the positions 2, 3, 4, 5 and 6. Similarly, 3,5-($CF_3$)2 means that two trifluoromethyl groups are bonded to the positions 3 and 5.

When n or m is zero, then X or Y are each represented by "H".

Examples of the benzyloxypyrimidine derivative of the formula (I) of the present invention are shown in the Table 1.

TABLE 1

| No. | R¹ | $Y_m$ | $X_n$ | G |
|---|---|---|---|---|
| I-1 | H | H | 3-CF$_3$ | O |
| I-2 | OCH2CH=CH2 | H | 3-CF$_3$ | O |
| I-3 | OCH2CH=CH2 | H | H | S |
| I-4 | OCH2CH=CH2 | 2-Cl | 3-CF$_3$ | O |
| I-5 | OCH2CH=CMe$_2$ | H | H | S |
| I-6 | Me | H | H | O |
| I-7 | Me | H | 3-Me | O |
| I-11 | Me | H | 3-CF$_3$ | O |
| I-12 | Me | H | 4-CF$_3$ | O |
| I-13 | Me | H | 3-CF$_3$ | S |
| I-14 | Me | 3-CF$_3$ | 3-CF$_3$ | O |
| I-15 | Me | 3-CF$_3$ | H | O |
| I-16 | OMe | H | 3-CF$_3$ | O |
| I-17 | OMe | 3-Me | 3-CF$_3$ | O |
| I-21 | OMe | 4-Me | 3-CF$_3$ | O |
| I-22 | OMe | 4-OMe | 3-CF$_3$ | O |
| I-23 | OMe | 4-CF$_3$ | 3-CF$_3$ | O |
| I-24 | OMe | 4-Cl | 3-CF$_3$ | O |
| I-25 | OEt | H | 3-CF$_3$ | O |
| I-26 | OEt | 2-Cl | 3-CF$_3$ | O |
| I-27 | OEt | 3-Cl | 3-CF$_3$ | O |
| I-31 | OEt | 4-Cl | 3-CF$_3$ | O |
| I-32 | SMe | H | 3-CF$_3$ | O |
| I-33 | SEt | H | 3-CF$_3$ | O |
| I-34 | SEt | H | 3-Cl | S |
| I-35 | CF$_3$ | H | 3-CF$_3$ | O |
| I-36 | Br | H | 3-CF$_3$ | O |
| I-37 | Br | H | 3-Cl | S |
| I-41 | Cl | H | 3-CF$_3$ | O |
| I-42 | Cl | H | 3-OCF$_3$ | O |
| I-43 | Cl | H | 3-OCH2CF$_3$ | O |
| I-44 | Cl | H | 3-OCH$_2$CF$_2$CF$_3$ | O |
| I-45 | Cl | H | 3-Br | O |
| I-46 | Cl | H | 3-Cl | O |
| I-47 | Cl | H | 3-I | O |
| I-51 | Cl | H | 2,3,4,5,6-F5 | O |
| I-52 | Cl | H | 3,5-(CF$_3$)$_2$ | O |
| I-53 | Cl | H | H | S |
| I-54 | F | H | 3-CF$_3$ | O |
| I-55 | I | H | 3-CF$_3$ | O |
| I-56 | CN | H | 3-CF$_3$ | O |
| I-57 | Cl | H | 2,4,6-Cl3 | O |
| I-58 | Cl | H | 3-SCF$_3$ | O |

The production of the benzyloxypyrimidine derivatives of the above formula (I) is generally conducted in a solvent, and examples of the solvent are as follows:

water;

organic acids such as formic acid, acetic acid, and propionic acid;

aromatic hydrocarbons such as benzene, toluene, xylene, and methylnaphthalene;

aliphatic hydrocarbons such as petroleum ether, pentane, hexane, heptane, and methylcyclohexane;

halogenated hydrocarbons such as methylene chloride, chloroform, carbon tetrachloride, and chlorobenzene;

alcohols such as methanol, ethanol, i-propanol, and t-butanol;

amides such as dimethylformamide, dimethylacetamide, and N-methyl-2-pyrrolidinone;

ethers such as diethyl ether, dimethoxyethane, diisopropyl ether, tetrahydrofuran, diglyme, and dioxane;

ketones such as acetone and methyl ethyl ketone;

as well as others including carbon disulfide, acetonitrile, ethyl acetate, acetic anhydride, pyridine, dimethyl sulfoxide, hexamethylphosphoric amide, and the like.

When the production process of the present invention is carried out in a solvent, the solvent may be used alone or in combination of two or more. Mixtures of the solvents incapable of forming a homogeneous phase may also be used. In such cases, the reaction may preferably be conducted in the presence of a phase transfer catalyst such as conventional quaternary ammonium salts or crown ether.

Individual reaction steps of the production process of the present invention all may advantageously be conducted in an inactive solvent or a mixture of inactive solvents.

The production process of the present invention may also be conducted in the presence of a basic compound, and examples of the basic compound are as follows:

alkaline metal carbonates such as sodium carbonate and potassium carbonate;

alkaline earth metal carbonates such as magnesium carbonate, calcium carbonate, and barium carbonate;

alkaline metal hydroxides such as sodium hydroxide and potassium hydroxide;

alkaline earth metal hydroxides such as magnesium hydroxide and calcium hydroxide;

alkaline earth metal oxides such as magnesium oxide and calcium oxide;

alkaline metals such as lithium, sodium and potassium and alkaline earth metals such as magnesium;

alkaline metal alkoxides such as sodium methoxide, sodium ethoxide and potassium t-butoxide;

alkaline metal hydrides such as sodium hydride and potassium hydride;

alkaline earth metal hydrides such as calcium hydride;

organometallic compounds of alkaline metals such as methyl lithium, ethyl lithium, n-butyl lithium, and phenyl lithium;

Grignard reagents such as methylmagnesium iodide, ethylmagnesium bromide, and n-butylmagnesium bromide;

organic copper compounds prepared from organometallic compounds of alkaline metals or Grignard reagents and copper(I) salts;

alkaline metal amides such as lithium diisopropylamide;

ammonium hydroxides optionally substituted at nitrogen with an alkyl group or an aralkyl group, such as aqueous ammonia, benzyl trimethyl ammonium hydroxide, and tetramethyl ammonium hydroxide; and organic amines such as methylamine, ethylamine, n-propylamine, benzylamine, ethanolamine, dimethylamine, benzylmethylamine, dibenzylamine, triethylamine, triethanolamine, and pyridine.

The benzyloxypyrimidine derivative of the formula (I) of the present invention can be synthesized in accordance with the following Reaction scheme I or II.

Reaction Scheme I

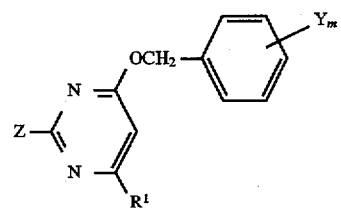

(II)

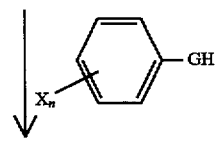

(III)

-continued
Reaction Scheme I

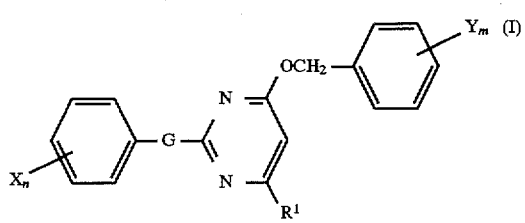

wherein R¹, X, Y, G, m, n and Z are as defined above.

Reaction Scheme II

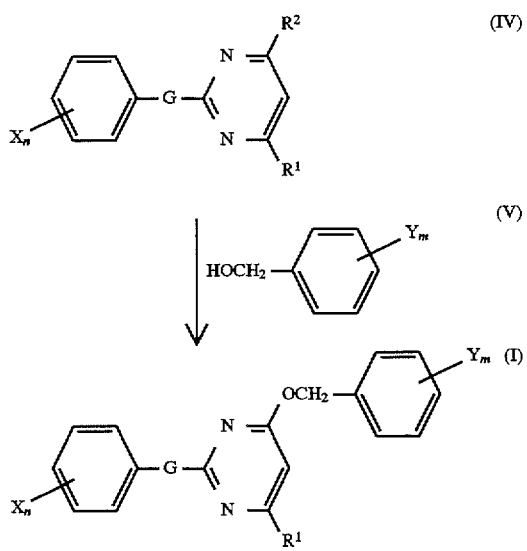

wherein R¹, R², X, Y, G, m and n are as defined above.

Reactions shown by the above schemes are nucleophilic displacement reaction occurred on the pyrimidine ring, thus may be conducted in accordance with a reaction sequence as below.

The derivative of the formula (I) may be synthesized in a solvent selected from amides such as dimethylformamide, dimethylacetamide and N-methyl-2-pyrrolidinone, ethers such as diethylether, dimethoxyethane, diisopropylether, tetrahydrofuran, diglyme and dioxane, and aromatic hydrocarbons such as benzene, toluene, xylene and methylnaphthalene or a mixture thereof, or in a two-phase system containing a phase transfer catalyst such as quaternary ammonium salts e.g. benzalkonium chloride and tetrabutyl ammonium chloride, in the presence of a basic compound, preferably at a temperature of −20° C. to 170° C., for a period of about 0.5 hour to 24 hours. Such basic compound may be a salt formed by substituting as a proton, the hydrogen atom bonded to an oxygen atom of the phenol compound of the formula (III) or of the benzyl alcohol compound of the formula (IV) or the hydrogen atom bonded to a sulfur atom of the thiophenol compound of the formula (III).

An iodide such as sodium iodide and potassium iodide or a crown ether such as 18-crown-6 and dibenzo-18-crown-6 may be added to the reaction system for a reaction accelerator.

Examples of the phenol compound of the formula (III) wherein G is O are 2,3,4,5,6-pentafluorophenol, 2,4,6-trichlorophenol, 3,5-bis(trifluoromethyl)phenol, 3-bromophenol, 3-chlorophenol, 3-iodophenol, 3-methylphenol, 3-(trifluoromethyl)phenol, 3-(trifluoromethoxy)phenol, 3-(2,2,2-trifluoroethoxy) phenol, 3-(2,2,2,3,3-pentafluoropropoxy)phenol, 3-trifluoromethylthio)phenol, and 4-(trifluoromethyl) phenol.

Examples of the thiophenol compound of the formula (III) wherein G is S are 3-chlorothiophenol and 3-(trifluoromethyl)thiophenol.

Examples of the benzyl alcohol compound of the formula (V) are benzyl alcohol, 2-chlorobenzyl alcohol, 3-chlorobenzyl alcohol, 3-methylbenzyl alcohol, 3-(trifluoromethyl)benzyl alcohol, 4-chlorobenzyl alcohol, 4-methylbenzyl alcohol, 4-methoxybenzyl alcohol, and 4-(trifluoromethyl)benzyl alcohol.

Examples of the 2-(leaving-group-substituted)-pyrimidine derivative of the above formula (II) are shown in Table 2.

TABLE 2

| No.   | R¹          | Y$_m$  | Z       |
|-------|-------------|--------|---------|
| II-1  | OCH₂CH=CH₂  | H      | MeSO₂   |
| II-2  | OCH₂CH=CH₂  | 2-Cl   | MeSO₂   |
| II-3  | OCH₂CH=CMe₂ | H      | MeSO₂   |
| II-4  | Me          | H      | MeSO₂   |
| II-5  | Me          | 3-CF₃  | MeSO₂   |
| II-6  | OMe         | H      | MeSO₂   |
| II-7  | OMe         | 3-Me   | MeSO₂   |
| II-11 | OMe         | 4-Me   | MeSO₂   |
| II-12 | OMe         | 4-OMe  | MeSO₂   |
| II-13 | OMe         | 4-CF₃  | MeSO₂   |
| II-14 | OMe         | 4-Cl   | MeSO₂   |
| II-15 | OEt         | H      | MeSO₂   |
| II-16 | OEt         | 2-Cl   | MeSO₂   |
| II-17 | OEt         | 3-Cl   | MeSO₂   |
| II-21 | OEt         | 4-Cl   | MeSO₂   |
| II-22 | CF₃         | H      | MeSO₂   |
| II-23 | Br          | H      | MeSO₂   |
| II-24 | Cl          | H      | MeSO₂   |
| II-25 | I           | H      | MeSO₂   |

Among 2-(leaving-group-substituted) pyrimidine derivatives of the formula (II), those in which Z is bonded to the pyrimidine ring by a sulfonyl group may be synthesized in accordance with the Reaction scheme III. In other words, 2-(substituted sulfonyl)pyrimidine derivatives of the formula (II-a) can be obtained by oxidizing the sulfur atom at the position 2 of 2-(substituted thio)pyrimidine derivatives of the formula (VI).

Reaction Scheme III

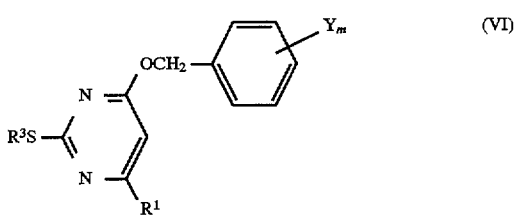

-continued
Reaction Scheme III

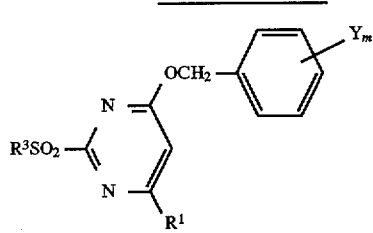
(II-a)

wherein $R^1$, Y and m are as defined above; and $R^3$ represents $C_1$–$C_4$ alkyl, $C_7$–$C_9$ aralkyl or aryl (generally $C_6$–$C_8$), preferably methyl, ethyl, benzyl, phenyl or 4-methylphenyl.

Among 2-(substituted sulfonyl)pyrimidine derivatives of the above formula (II-a), those in which $R^3$ represents methyl (Me) are identical with 2-(leaving-group-substituted) pyrimidine derivatives of the formula (II) in which Z represents methylsulfonyl ($MeSO_2$).

Examples of an oxidizing agent which may be suitably used for the above oxidation are peracids, sodium hypochlorite, chlorine, potassium permanganate and sodium tungstate.

Among the peracids, peracetic acid, perbenzoic acid, meta-chloroperbenzoic acid and perphthalic acid are preferable.

Peracetic acid may be in situ produced in the reaction vessel by adding hydrogen peroxide to an acetic acid solution of the compound of the formula (VI).

Solvents which may be suitably used in the above oxidation include halogenated alkyls (e.g., dichloromethane and chloroform), esters, aromatic hydrocarbons, lower fatty acids and water. When an oxidizing agent requires water (e.g., chlorine), water should be used as a solvent.

This oxidation may be carried out at a temperature of from 5° C. to the reflux point of the solvent (when a solvent is used).

Specifically, oxidation may be conducted as follows. Compounds II-1 to II-25 in the Table 2 may be each synthesized as follows.

The 2-(substituted thio)pyrimidine derivative of the formula (VI) wherein $R^1$, Y and m are as shown in the Table 2 and $R^3$ represents methyl and chloroform are stirred while cooling with iced water. Then, meta-chloroperbenzoic acid is added thereto in an molar amount of approximately twice on the basis of the compound of the formula (VI). Thereafter, the resulting solution is stirred for 1 to 4 hours at a temperature of 1° to 30° C.

The reaction mixture is partitioned by using aqueous saturated sodium hydrogen carbonate. The obtained organic layer is washed successively with aqueous sodium hydrogen sulfite and aqueous saturated sodium chloride, then dried over anhydrous sodium sulfate. Thereafter, the solvent is distilled off to afford a crude product, which is then purified on column chromatography, whereby the Compound II-1 to II-25 can be obtained.

Alternatively, the 2-(substituted thio)pyrimidine derivatives of the formula (VI) wherein $R^1$ Y and m are as shown in the Table 2 and $R^3$ represents methyl is dissolved in acetic acid and, to the resulting solution, hydrogen peroxide is added so as to produce peracetic acid required for the oxidation in a reaction vessel, whereby the corresponding compound of the formula (II-a) can be obtained. In this case, reaction may be conducted preferably for a period of 2 to 4 hours at a temperature of 60° C. to the reflux point.

The 2-(substituted thio)pyrimidine derivative of the above formula (VI) can be synthesized by reacting a 2-(substituted thio)-4(or 6)-halogenopyrimidines or a 2-(substituted thio)-4,6-dihalogenopyrimidines of the formula (VII) with a benzyl alcohol compound of the formula (V) in accordance with the Reaction scheme IV.

Reaction Scheme IV

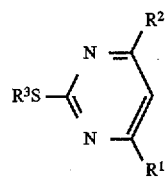

wherein $R^1$, $R^2$, $R^3$, y, and m are as defined above.

It has been reported a preparation of 4-benzyloxy-2-(methylsulfonyl)pyrimidine which is a member of the compounds of the above formula (II-a), by reacting the starting 4-chloro-2-(methylthio)pyrimidine with benzyl alcohol in accordance with the above Reaction scheme IV to synthesize 4-benzyloxy-2-(methylthio)pyrimidine, and then oxidizing with meta-chloroperbenzoic acid in accordance with the above Reaction scheme III (Tetrahedron Letters, 1971, 2867 to 2870). That is, the compound of the formula (VII) is benzyloxylated to obtain the compound of the formula (VI).

This synthesis route is suitable for synthesis of the compound of the formula (I) which has no sulfide bond such as one wherein $R^1$ is not $C_1$–$C_4$ alkylthio or G is O.

For synthesis of the compound of the formula (I) which has a sulfide bond, a route via the compound of the formula (II) wherein Z is a halogen or a route via the compound of the formula (IV) is suitable.

Examples of the compound of the formula (VII) are shown in Table 3.

TABLE 3

| No. | $R^1$ | $R^2$ | $R^3$ |
|---|---|---|---|
| VII-1 | $OCH_2CH=CH_2$ | Cl | Me |
| VII-2 | $OCH_2CH=CMe_2$ | Cl | Me |
| VII-3 | Me | Cl | Me |
| VII-4 | OMe | Cl | Me |
| VII-5 | OEt | Cl | Me |
| VII-6 | $CF_3$ | Cl | Me |
| VII-7 | Br | Br | Me |
| VII-8 | Cl | Cl | Me |
| VII-9 | I | I | Me |

Among the compounds of the formula (VII), 2-(substituted thio)-4,6-dihalogenopyrimidine derivatives can be synthesized by using the following process.
Process (a1)

A malonic ester is cyclo-condensed with (S-substituted) isothiourea to obtain a 2-(substituted thio)-4,6-dihydroxypyrimidine derivative.

The same derivatives may be synthesized by the following process (a2) in place of the above process (a1).

Process (a2)

A malonic ester is cyclo-condensed with thiourea to obtain 2-mercapto-4,6-dihydroxypyrimidine.

Then, the 2-mercapto group is converted to 2-(substituted thio) group in the presence of a basic compound. This process is suitable for the compound in which the substituent in the 2-(substituted thio) group is $C_1$–$C_4$ alkyl or $C_7$–$C_9$ aralkyl.

Each hydroxyl bonded to the positions 4 and 6 on the pyrimidine ring of the compound obtained by the process (a1) or (a2) is then converted to a halogen:

Process (b1)

Hydroxyl is converted to a halogen by using phosphorus oxychloride (identical with phosphoryl chloride), phosphorus pentachloride, or phosphorus oxybromide (identical with phosphoryl bromide).

Further, chlorine at the position 4 and/or 6 may be converted to iodine through nucleophilic displacement by using potassium iodide or aqueous concentrated hydroiodic acid.

Among the compounds of the formula (VII), 2-(substituted thio)-4(or 6)-halogenopyrimidine derivatives in which a substituent is ether-bonded to the position 4 and/or 6 on the pyrimidine ring can be synthesized as follows:

Process (c1)

A halogen at the position 4 or 6 on the pyrimidine ring of the compound which is obtained from the process (b1) is etherified through nucleophilic displacement in the presence of a basic compound.

Process (d1)

Either one of halogens at the positions 4 and 6 on the pyrimidine ring of the compound which is obtained from the process (b1) is converted to hydroxyl.

Process (e1)

Hydroxyl of the compound which is obtained from the process (d1) is etherified.

Among the compounds of the formula (VII), the 2-(substituted thio)pyrimidine derivatives in which $R^1$ represents a substituent linked by carbon-carbon bond at the position 4 or 6 on the ring or hydrogen can be synthesized as follows:

Process (a3)

A compound containing a 1,3-dicarbonyl group {one of the carbonyl groups is derived from a carboxylic ester and the other is derived from a formyl group (or acetal thereof) or an acyl group (or ketal thereof)} may be cyclo-condensed with a (S-substituted)thiourea to obtain a 2-(substituted thio)-4(or 6)-hydroxypyrimidine derivative.

The same derivatives may be synthesized by the following process (a4) in place of the above process (a3).

Process (a4)

A compound containing a 1,3-dicarbonyl group {one of the carbonyl groups is derived from a carboxylic ester and the other is derived from a formyl group (or acetal thereof) or an acyl group (or ketal thereof)} may be cyclo-condensed with thiourea to obtain a 2-mercapto-4-(or 6)-hydroxypyrimidine derivative.

Then, 2-mercapto group is converted to 2-(substituted thio) group in the presence of a basic compound.

This process is suitable for the compounds in which the substituent in the 2-(substituted thio) group is $C_1$–$C_4$ alkyl or $C_7$–$C_9$ aralkyl.

Then, hydroxyl bonded to the position 4 or 6 on the pyrimidine ring of the compound obtained by the process (a3) or (a4) may be converted to a halogen:

Process (b2)

Hydroxyl may be converted to a halogen by using phosphorus oxychloride (identical with phosphoryl chloride), phosphorus pentachloride, or phosphorus oxybromide (identical with phosphoryl bromide).

Synthesis processes may be more specifically described in the following.

Compounds which contain on the pyrimidine ring thereof, hydroxyl to be afterwards converted to chlorine or bromine and which are usable as starting materials of the compounds of the formula (VII) can be synthesized by using the synthesis processes (a1) or (a3) in a manner described in the section (1) or section (2) below.

(1) 0.1 mol of methyl acetoacetate or methyl trifluoroacetoacetate, 0.1 mol of methylisothiourea sulfate (2-methyl-2-thiopseudourea sulfate) and 0.1 mol of sodium methoxide are reacted with one another in 500 ml of methyl alcohol at room temperature for overnight.

Then, the reaction mixture is cooled with iced water and 0.1 mol of hydrochloric acid is added thereto.

After insoluble matter is filtered off, the solvent is distilled off from the filtrate to afford a crude product, which may be then recrystallized to obtain a purified product.

(2) 0.1 mol of ethyl 3,3-diethoxypropionate, ethyl acetoacetate, ethyl propionylacetate, ethyl 2,2-dimethylpropionylacetate, ethyl benzoylacetate, ethyl trifluoroacetoacetate or diethyl malonate, 0.1 mol of methylisothiourea sulfate (2-methyl-2-thiopseudourea sulfate) and 0.1 mol of sodium ethoxide are reacted with one another in 500 ml of ethyl alcohol at reflux point for 4 hours.

The reaction mixture is allowed to cool to room temperature, and then, while further cooling with iced water, 0.1 mol of hydrochloric acid is added thereto.

After insoluble matter is filtered off, the solvent is distilled off from the filtrate to afford a crude product, which may be then recrystallized to obtain a purified product.

Each of the Compounds VII-8 and VII-7 can be synthesized by using the process (b1).

50 ml of phosphorus oxychloride (identical with phosphoryl chloride) or phosphorus oxybromide (identical with phosphoryl bromide) is reacted with 0.1 mol of 4,6-dihydroxy-2-methylthiopyrimidine while stirring at a temperature of 70° C. to 80° C. for 7 hours.

Excess phosphorus oxychloride or phosphorus oxybromide is distilled off under reduced pressure from the reaction mixture.

The residue is redissolved in chloroform and washed successively with aqueous sodium hydrogen carbonate and water. After dried over sodium sulfate, the solvent is distilled off to afford a crude product, which may be then purified on column chromatography to obtain a purified product.

Compound VII-9 can be synthesized by heating the Compound VII-8 at about 70° C. for about 13 hours in the presence of an excessive amount of aqueous 57% hydroiodic acid.

The following procedure may be mentioned as the process (b2).

0.1 mol of a compound containing on the pyrimidine ring, hydroxyl to be afterwards converted to chlorine is reacted with 50 ml of phosphorus oxychloride while stirring at a temperature of 70° C. to 80° C. for 7 hours.

Excess phosphorus oxychloride is distilled off under reduced pressure from the reaction mixture.

The residue is redissolved in chloroform and washed successively with aqueous sodium hydrogen carbonate and water. After dried over sodium sulfate, the solvent is distilled off to afford a crude product, which may be then purified on column chromatography to obtain a purified product.

The following procedure may be mentioned as the process (c1).

Compound VII-8 is prepared by nucleophilic substitution for one chlorine of Compound VII-8 with an equimolar amount of sodium allylalkoxide or sodium 3-methyl-2-buten-1-oxide in dimethylformamide at room temperature for overnight.

Compound VII-8 is prepared by nucleophilic substitution for one chlorine of Compound VII-8 with an equimolar amount of sodium methoxide or sodium ethoxide in tetrahydrofuran at room temperature for 30 minutes.

A used amount of Compound VII-8 is predetermined, and 60% sodium hydride in an equimolar amount to one chlorine of Compound VII-8 is dissolved under water cooling into an excess amount of propanol, butanol, 1-methylethanol, or 2,2,2-trifluoroethanol which also serves as a solvent. Then Compound VII-8 is added to conduct the reaction at a temperature of 35° C. to 45° C. for 4 hours, thereby carrying out nucleophilic substitution for one chlorine of the Compound VII-8.

in the above processes, when it is intended to obtain a compound having a single ether-bonded $R^1$, an alcohol is used singly.

After the solvent and alcohol are distilled off from the reaction mixture under reduced pressure, ether is poured into the residue, and the mixture is washed with water and then dried over sodium sulfate.

Ether is distilled off to afford a crude product, which may then be purified on column chromatography to obtain a purified product.

Other compounds of the formula (II-a) can also be synthesized in a similar manner.

When benzyloxypyrimidine derivatives of the above formula (I) are synthesized in accordance with the above Reaction scheme II, among immediately preceding intermediates, 2-(substituted or unsubstituted phenoxy)-4(or 6)-halogenopyrimidine or 2-(substituted or unsubstituted phenylthio)-4(or 6)-halogenopyrimidine of the above formula (IV-b) may be synthesized in accordance with the Reaction scheme V by nucleophilic substitution for one halogen of 2-(substituted or unsubstituted phenoxy)-4,6-dihalogenopyrimidine or 2-(substituted or unsubstituted phenylthio)-4,6-dihalogenopyrimidine of the above formula (IV-a) with an alcohol or thiol compound of the formula (VIII).

Reaction Scheme V

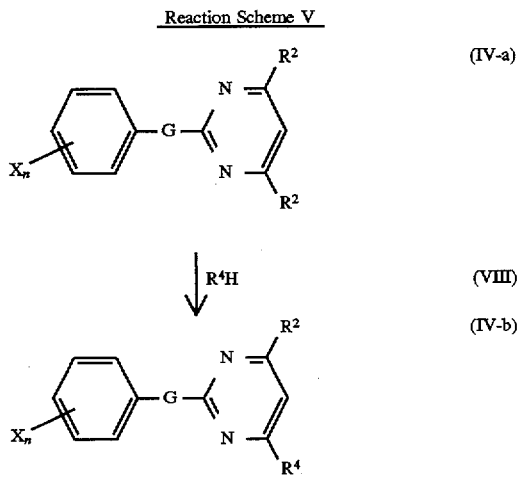

wherein $R^2$, G, X, and n are as defined above; and $R^4$ represents $C_1$-$C_4$ alkoxy, $C_1$-$C_4$ haloalkoxy, $C_3$-$C_5$ alkenyloxy, C1-$C_4$ alkylthio, or cyano.

The compound of the formula (IV-a), a phenoxy or thiophenoxy compound which is unsubstituted or substituted at the position 2 may be produced by oxidizing $R^3S$ of the compound of the formula (VII) wherein $R^1$ is a halogen (preferably chlorine, bromine, or iodine) such as Compounds VII-7 and VII-8 to $R^3SO_2$, and then carrying out nucleophilic substitution with the compound of the formula (III).

Also, the compound of the formula (IV-a) may be produced by nucleophilic substitution for a halogen at the position 2 of 2,4,6-trihalopyrimidine (preferably 2,4,6-trichloropyrimidine) with the compound of the formula (III).

Examples of the compound of the formula (III) are 2-propenol, 3-methyl-2-buten-1-ol, methanol, ethanol, methanethiol, and ethanethiol.

The compound of the formula (IV-b) compound may be obtained by nucleophilic substitution for one halogen in the compound of the formula (IV-a) in the presence of an basic compound or after hydrogen bonded to oxygen or sulfur in the compound of the formula (VIII) is substituted with a counter ion such as sodium.

The compounds of the formulae (IV-a) and (IV-b) are both used as the starting compound in the Reaction scheme II.

Further, from the compound of the formula (I) wherein $R^1$ is a halogen, the corresponding compound of the formula (I) may be derived by nucleophilic substitution for the halogen with the compound of the formula (VIII). Since, this process does not include oxidation in the preceding production of the starting materials, the process is suitable for synthesis of the compound of the formula (I) having a sulfide bond.

Since all of the reactions represented by the Reaction schemes I, II, IV, and V, the reaction of the compound of the formula (III) with the compound of the formula (VII) (for production of the compound of the formula (IV-a)), and the reaction of the compound of the formula (I) wherein $R^1$ is a halogen with the compound of the formula (VIII) described above are nucleophilic displacement reaction occurred on the pyrimidine ring, almost the same reaction conditions may be used including the choice of base, solvent, and reaction temperature and time.

Although the derivative of the formula (I) may be applied as it is, it may be generally applied after formulated with an adjuvant into various forms of compositions such as powders, wettable powders, granules or emulsifiable concentrates.

The composition is usually formulated in such a way that it contains one or more of the derivatives of the formula (I) at an amount of 0.1 to 95% by weight, preferably 0.5 to 90% by weight, more preferably 2 to 70% by weight.

As adjuvants including carriers, diluents and surface active agents, suitable solid carriers include talc, kaolin, bentonite, diatomaceous earth, white carbon, clay and the like. Suitable liquid diluents include water, xylene, toluene, chlorobenzene, cyclohexane, cyclohexanone, dimethylsulfoxide, dimethylformamide, alcohol and the like.

Surface active agents may be properly selected depending upon their effects, and suitable emulsifying agents include polyoxyethylene alkyl aryl ether, and polyoxyethylene sorbitan monolaurate and the like. Suitable dispersing agents include lignin sulfonate, dibutylnaphthalene sulfonate and the like. Suitable wetting agents include alkyl sulfonates, alkylphenyl sulfonates and the like.

The above mentioned compositions include those which are to be applied as such and those which are to be applied after diluted to a proper concentration by using a diluent such as water. When applied in a diluted form, the derivative of the formula (I) is contained preferably at a concentration of 0.001 to 1.0% by weight. Application dose of the derivative of the formula (I) is generally 0.0to 10 kg/ha, preferably 0.05 to 5 kg/ha.

The concentrations and the application doses defined above are varied depending on dosage forms, time of application, way of application, application sites, crops to be treated and the like. Thus, modifications thereof are possible without limited to the above defined range. Further, the derivatives of the formula (I) may be used in combination with other active ingredients such as e.g., fungicides, insecticides, acaricides and herbicides.

EXAMPLES

The benzyloxypyrimidine derivative, the processes for producing the derivative and the use of the derivative according to the present invention will be more specifically described by way of synthesis examples, formulation examples and test examples set forth in the following.

It will be also understood that the present invention should be considered as not limited to the details of these examples without departing from the scopes of the present invention.

Synthesis Example 1

Synthesis of 4-benzyloxy-2-[3-(trifluoromethyl)phenoxy] pyrimidine (Compound I-1)

3-(Trifluoromethyl)phenol (0.280 g, 0.00157×1.1 mol) was dissolved in tetrahydrofuran, and then sodium hydride (0.66 g (60% in mineral oil), 0.00157×1.05 mol) was added thereto to prepare a phenoxide.

4-Benzyloxy-2-(methylsulfonyl)pyrimidine (0.415 g, 0.00157 mol) was added thereto and the resulting solution was stirred for about 2 hours at room temperature.

The reaction solution was poured into water and extracted with ethyl acetate. The obtained organic phase was washed successively with aqueous saturated sodium hydrogen carbonate and aqueous saturated sodium chloride, then dried over anhydrous sodium sulfate and thereafter concentrated. The concentrate was purified on silica gel column chromatography no obtain the end product. Yield: 0.40 g (74%).

Synthesis Example 2

Synthesis of 4-benzyloxy-6-methyl-2-(phenoxy)pyrimidine (Compound I-6)

Phenol (0.23 g, 0.00162×1.5 mol) was dissolved in tetrahydrofuran, and then sodium hydride (0.071 g (60% in mineral oil), 0.00162×1.1 mol) was added thereto to prepare a phenoxide.

4-Benzyloxy-6-methyl-2-(methylsulfonyl)pyrimidine (Compound II-4) (0.45 g, 0.00162 mol) was added thereto and the resulting solution was allowed to react for about 2 hours at room temperature. The reaction solution was poured into water and extracted with ethyl acetate to separate an organic phase. The obtained organic phase was washed successively with aqueous saturated sodium hydrogen carbonate and aqueous saturated sodium chloride, then dried over anhydrous sodium sulfate and thereafter concentrated. The concentrate was purified on silica gel column to obtain the end product.

Yield: 0.37 g (78%).

Synthesis Example 3

Synthesis of 4-methoxy-6-(4-methylbenzyloxy)-2-[3-(trifluoromethyl)phenoxy]pyrimidine (Compound I-21)

3-(Trifluoromethyl)phenol (0.21 g, 0.00115×1.1 mol) was dissolved in tetrahydrofuran, and then sodium hydride (0.050 g (60% in mineral oil), 0.00115×1.05 mol) was added thereto to prepare a phenoxide.

4-Methoxy-6-(4-methylbenzyloxy)-2-(methylsulfonyl) pyrimidine (Compound II-11) (0.354 g, 0.00115 mol) was added thereto and the resulting solution was stirred for about 2 hours at room temperature.

The reaction solution was poured into water and extracted with ethyl acetate. The obtained organic phase was washed successively with aqueous saturated sodium hydrogen carbonate and aqueous saturated sodium chloride, then dried over anhydrous sodium sulfate and thereafter concentrated. The concentrate was purified on silica gel column chromatography to obtain the end product.

Yield: 0.30 g (67%).

Synthesis Example 4

Synthesis of 4-benzyloxy-6-trifluoromethyl-2-[3-(trifluoromethyl)phenoxy]pyrimidine (Compound I-35)

3-(Trifluoromethyl)phenol (1.46 g, 0.0090×1.0 mol) was dissolved in tetrahydrofuran, and then sodium hydride (0.379 g (60% in mineral oil), 0.0090×1.05 mol) was added thereto under cooling with ice to prepare a phenoxide.

4-Benzyloxy-2-methylsulfonyl-6-(trifluoromethyl) pyrimidine (Compound II-22) (3.0 g, 0.0090 mol) which had been dissolved in tetrahydrofuran was added thereto.

After allowed to react for about 2 hours at room temperature, the reaction solution was poured into water and extracted with ethyl acetate.

The obtained organic phase was washed with aqueous saturated sodium chloride and then dried over anhydrous sodium sulfate. After the solvent was distilled off, the residue was purified on silica gel column chromatography to obtain the end product.

Yield: 2.2 g (59%).

Synthesis Example 5

Synthesis of 4-benzyloxy-6-bromo-2-[3-(trifluoromethyl) phenoxy]pyrimidine (Compound I-36)

3-(Trifluoromethyl)phenol (0.449 g, 0.00252×1.1 mol) was dissolved in tetrahydrofuran, then sodium hydride (0.106 g (60% in mineral oil), 0.00252×1.05 mol) was added thereto to prepare a phenoxide.

4-Benzyloxy-6-bromo-2-(methylsulfonyl)pyrimidine (Compound II-23) (0.865 g, 0.00252 mol) was added thereto and the resulting solution was stirred for about 2 hours at room temperature.

The reaction solution was poured into water and extracted with ethyl acetate. The obtained organic phase was washed successively with aqueous saturated sodium hydrogen carbonate and aqueous saturated sodium chloride, then dried over anhydrous sodium sulfate and thereafter concentrated. The concentrate was purified on silica gel column chromatography to obtain the end product.

Yield: 0.60 g (56%).

Synthesis Example 6

Synthesis of 4-benzyloxy-6-chloro-2-(3-chlorophenoxy) pyrimidine (Compound I-46)

meta-Chlorophenol (0.24 g, 0.00167×1.0 mol) was dissolved in tetrahydrofuran, and then sodium hydride (0.067 g (60% in mineral oil), 0.00167×1.0 mol) was added thereto to prepare a phenoxide.

4-Benzyloxy-6-chloro-2-(methylsulfonyl)pyrimidine (Compound II-24) (0.50 g, 0.00167 mol) was added thereto and the resulting solution was allowed to react for about 2 hours at room temperature.

The reaction solution was poured into water and extracted with ethyl acetate. The obtained organic phase was washed successively with aqueous saturated sodium hydrogen carbonate and aqueous saturated sodium chloride, then dried over anhydrous sodium sulfate and thereafter concentrated. The concentrate was purified on silica gel column chromatography to obtain the end product. Yield: 0.53 g (91%). Melting point: 64°–67° C.

Synthesis Example 7

Synthesis of 4-benzyloxy-6-iodo-2-[3-(trifluoromethyl) phenoxy]pyrimidine (Compound I-55)

3-(Trifluoromethyl)phenol (0.29 g, 0.0018×1.1 mol) was dissolved in tetrahydrofuran, and then sodium hydride (0.076 g (60% in mineral oil), 0.0018×1.05 mol) was added thereto to prepare a phenoxide.

4-Benzyloxy-6-iodo-2-(methylsulfonyl)pyrimidine (Compound II-25) (0.70 g, 0.0018 mol) was added thereto and the resulting solution was stirred for about 2 hours at room temperature.

The reaction solution was poured into water and extracted with ethyl acetate. The obtained organic phase was washed successively with aqueous saturated sodium hydrogen carbonate and aqueous saturated sodium chloride, then dried over anhydrous sodium sulfate and thereafter concentrated. The concentrate was purified on silica gel column chromatography to obtain the end product.

Yield: 0.60 g (71%).

Synthesis Example 8

Synthesis of 4-benzyloxy-6-methyl-2-[3-(trifluoromethyl) phenylthio]pyrimidine (Compound I-13)

Benzyl alcohol (135 mg, 1.25×1.0 mmol) and 4-chloro-6-methyl-2-[3-(trifluoromethyl)phenylthio]pyrimidine (180 mg, 1.25 mmol) were dissolved in toluene and cooled with ice.

After 60% sodium hydride (55 mg, 1.25×1.1 mmol) was added thereto, the resulting solution was stirred overnight at room temperature.

The reaction solution was poured into water and extracted with ethyl acetate to separate an organic phase. The obtained organic phase was washed with aqueous saturated sodium chloride, then dried over anhydrous sodium sulfate and thereafter concentrated. The concentrate was purified on silica gel column chromatography to obtain the end product.

Yield: 0.28 g (81%).

Synthesis Example 9

Synthesis of 4-benzyloxy-6-methylthio-2-[3-(trifluoromethyl)phenoxy]pyrimidine (Compound I-32)

4-Chloro-6-methylthio-2-[3-(trifluoromethyl)phenoxy] pyrimidine 1.6 g, 0.0050 mol) and benzyl alcohol (0.54 g, 0.0050×1.0 mol) were dissolved in a mixed solvent of tetrahydrofuran and dimethylformamide (1:2 (v/v)).

Sodium hydride (0.21 g (60% in mineral oil), 0.0050× 1.05 mol) 1.05 mol) and potassium iodide (0.42 g, 0.0050× 0.5 mol) were added thereto and the resulting solution was refluxed for about 1 hour.

The reaction solution was poured into water and extracted with ethyl acetate. The obtained organic phase was washed successively with aqueous saturated sodium hydrogen carbonate and aqueous saturated sodium chloride, then dried over anhydrous sodium sulfate and thereafter concentrated. The concentrate was purified on silica gel column chromatography to obtain the end product.

Yield: 1.1 g (57%).

NMR data of the compounds synthesized in the above examples 1 to 9 as well as of those synthesized in a similar manner to these examples are shown in the Table 4.

TABLE 4

| No. | $^1$H-NMR (60 MHZ, CDCl$_3$, δ) |
|---|---|
| I-1 | 5.13(2H, s), 6.45(1H, d, J=5.5Hz), 7.20(5H, s), 7.2–7.7(4H, m), 8.25(1H, d, J=5.5Hz) |
| I-2 | 4.5–4.9(2H, m), 5.1–5.6(2H, m), 5.19(2H, s), 5.4–6.2(1H, m), 5.79(1H, s), 7.20(5H, s), 7.1–7.6(4H, m) |
| I-3 | 4.7–5.0(2H, m), 5.1–6.3(3H, m), 5.33(2H, s), 5.76(1H, s), 7.1–7.5(10H, m) |
| I-4 | 4.5–4.9(2H, m), 5.1–5.6(2H, m), 5.30(2H, s), 5.4–6.2(1H, m), 5.75(1H, s), 7.0–7.7(8H, m) |
| I-5 | 1.60(3H, s), 1.67(3H, s), 4.65(2H, d, J=7Hz), 5.1–5.5(1H, m), 5.27(2H, s), 5.65(1H, s), 7.1–7.7(10H, m) |
| I-6 | 2.30(3H, s), 5.12(2H, s), 6.22(1H, s), 7.17(10H, s) |
| I-7 | 2.31(6H, s), 5.22(2H, s), 6.14(1H, s), 6.6–7.5(4H, m), 7.23(5H, s) |
| I-11 | 2.33(3H, s), 5.14(2H, s), 6.27(1H, s), 6.9–7.6(4H, m), 7.19(5H, s) |
| I-12 | 2.33(3H, s), 5.15(2H, s), 6.29(1H, s), 6.9–7.4(7H, m), 7.55(2H, d, J=8.9Hz) |
| I-13 | 2.30(3H, s), 5.00(2H, s), 6.23(1H, s), 7.0–8.0(9H, m) |
| I-14 | 2.25(3H, s), 5.04(2H, s), 6.20(1H, s), 6.9–7.7(8H, m) |
| I-15 | 2.17(3H, s), 5.21(2H, s), 6.24(1H, s), 6.8–7.6(9H, m) |
| I-16 | 3.86(3H, s), 5.15(2H, s), 5.74(1H, s), 7.1–7.6(4H, m), 7.20(5H, s) |
| I-17 | 2.25(3H, s), 3.89(3H, s), 5.13(2H, s), 5.76(1H, s), 6.9–7.7(8H, m) |
| I-21 | 2.27(3H, s), 3.85(3H, s), 5.09(2H, s), 5.73(1H, s), 6.9–7.5(4H, m), 7.08(4H, s) |
| I-22 | 3.65(3H, s), 3.86(3H, s), 5.04(2H, s), 5.76(1H, s), 6.65(2H, d, J=8.5Hz)., 7.67(2H, d, J=8.5Hz), 7.0–7.6(4H, m) |
| I-23 | 3.83(3H, s), 5.16(2H, s), 5.73(1H, s), 7;1–7.7(8H, m) |
| I-24 | 3.85(3H, s), 5.06(2H, s), 5.75(1H, s), 7.0–7.7(8H, m) |
| I-25 | 1.30(3H, t, J=6.9Hz), 4.25(2H, q, J=6.9Hz), 5.10(2H, s), 5.67(1H, s), 7.0–7.5(4H, m), 7.14(5H, s) |
| I-26 | 1.30(3H, t, J=6.9Hz), 4.30(2H, q, J=6.9Hz), 5.09(2H, s), 5.70(1H, s), 6.9–7.7(8H, m) |
| I-27 | 1.29(3H, t, J=6.9Hz), 4.31(2H, q, J=6.9Hz), 5.21(2H, s), 5.73(1H, s), 6.9–7.6(8H, m) |
| I-31 | 1.29(3H, t, J=6.9Hz), 4.26(2H, q, J=6.9Hz), 5.05(2H, s), 5.74(1H, s), 6.9–7.6(8H, m) |
| I-32 | 2.48(3H, s), 5.16(2H, s), 6.30(1H, s), 7.0–7.6(4H, m), 7.21(5H, s) |
| I-33 | 1.31(3H, t, J=6.9Hz), 3.05(2H, q, J=6.9Hz), 5.14(2H, s), 6.27(1H, s), 7.0–7.6(4H, m), 7.20(5H, s) |
| I-34 | 1.25(3H, t, J=6.9Hz), 3.00(2H, q, J=6.9Hz), 5.21(2H, s), 6.23(1H, s), 7.0–7.7(9H, m) |
| I-35 | 5.21(2H, s), 6.83(1H, s), 7.0–7.6(4H, m), 7.20(5H, s) |
| I-36 | 5.20(2H, s), 6.65(1H, s), 7.1–7.6(9H, m) |
| I-37 | 5.19(2H, s), 6.63(1H, s), 7.01–7.6(9H, m) |
| I-41 | 5.19(2H, s), 6.49(1H, s), 7.0–7.6(4H, m), 7.22(5H, s) |
| I-42 | 5.17(2H, s), 6.46(1H, s), 6.9–7.6(9H, m) |
| I-43 | 4.19(2H, q, J=8.5Hz), 5.15(2H, s), 6.4–7.5(10H, m) |
| I-44 | 4.31(2H, t, J=12Hz), 5.17(2H, s), 6.4–7.5(10H, m) |
| I-45 | 5.18(2H, s), 6.44(1H, s), 6.8–7.5(4H, m), 7.21(5H, s) |
| I-46 | 5.18(2H, s), 6.43(1H, s), 6.8–7.4(9H, m) |
| I-47 | 5.16(2H, s), 6.40(1H, s), 6.9–7.7(4H, m), 7.20(5H, s) |
| I-51 | 5.21(2H, s), 6.50(1H, s), 7.20(5H, s) |
| I-52 | 5.17(2H, s), 6.49(1H, s), 7.18(5H, s), 7.5–7.9(3H, m) |
| I-53 | 5.30(2H, s), 6.30(1H, s), 7.0–7.7(10H, m) |
| I-54 | 5.23(2H, s), 6.4–7.5(10H, m) |
| I-55 | 5.09(2H, s), 6.90(1H, s), 7.0–7.7(9H, m) |
| I-56 | 5.19(2H, s), 6.4–7.7(10H, m) |
| I-57 | 5.18(2H, s), 6.48(1H, s), 6.9–7.6(7H, m) |
| I-58 | 5.16(2H, s), 6.44(1H, s), 7.0–7.6(9H, m) |

Reference Synthesis Example 1

Synthesis of 4-benzyloxy-6-methyl-2-(methylsulfonyl)pyrimidine (Compound II-4)

(1) Synthesis of 4-benzyloxy-6-methyl-2-(methylthio)pyrimidine

Benzyl alcohol (1.86 g, 0.0086×2.0 mol) was dissolved in tetrahydrofuran, and then sodium hydride (0.43 g (60% in mineral oil), 0.0086×1.25 mol) was added thereto to prepare an alkoxide.

4-Chloro-6-methyl-2-(methylthio)pyrimidine (1.5 g, 0.0086 mol) was added thereto and the resulting solution was stirred for about 3 hours at room temperature. The reaction solution was poured into water and extracted with ethyl acetate.

The obtained organic phase was washed with aqueous saturated sodium chloride, then dried over anhydrous sodium sulfate and thereafter concentrated. The concentrate was purified on silica gel column chromatography to obtain the end product.

Yield: 1.18 g.

NMR data are shown in the Table 5 below Compound VI-4).

(2) Synthesis of the Compound II-4 4-Benzyloxy-6-methyl-2-(methylthio)pyrimidine (0.90 g, 0.00365 mol) was dissolved in chloroform, then meta-chloroperbenzoic acid (1.8 g, 0.00365×2.0 mol) was added thereto while cooling with ice and the resulting solution was allowed to react for about 2 hours at room temperature.

The reaction solution was poured into aqueous saturated sodium hydrogen carbonate and shaken. The organic phase was separated, then washed successively with aqueous sodium hydrogen sulfite and aqueous saturated sodium chloride and thereafter dried over anhydrous sodium sulfate. After filtration and concentration, the concentrate was purified on silica gel column chromatography to obtain 4-benzyloxy-6-methyl-2-(methylsulfonyl)pyrimidine (Compound II-4).

Yield: 0.70 g. Melting point: 57°–60° C.

Reference Synthesis Example 2

Synthesis of 4-benzyloxy-2-methylsulfonyl-6-(trifluoromethyl)pyrimidine (Compound II-22)

(1) Synthesis of 4-benzyloxy-2-methylthio-6-(trifluoromethyl)pyrimidine

4-Chloro-2-methylthio-6-(trifluoromethyl)pyrimidine (2.28 g, 0.010 mol) and benzyl alcohol (1.19 g, 0.0010×1.1 mol) were dissolved in tetrahydrofuran, then sodium hydride (0.44 g (60% in mineral oil), 0.010×1.1 mol) was added thereto and the resulting solution was refluxed for about 7 hours.

After allowed to cool to room temperature, the reaction solution was poured into water and extracted with ethyl acetate. The obtained organic phase was washed with aqueous saturated sodium chloride, dried over anhydrous sodium sulfate and thereafter concentrated. The concentrate was heated under reduced pressure in a tubular oven to remove off the residual benzyl alcohol and the like, whereby 4-benzyloxy-2-methylthio-6-(trifluoromethyl)pyrimidine was obtained.

Yield: 3.0 g.

(2) Synthesis of the Compound II-22

4-Benzyloxy-2-methylthio-6-(trifluoromethyl)pyrimidine, without further purification, was dissolved in chloroform, and then meta-chloroperbenzoic acid (4.93 g, 0.0010×2.0 mol) was added thereto while cooling with ice. The resulting solution was allowed to react for about 2 hours at room temperature.

The reaction solution was washed successively with aqueous saturated sodium hydrogen carbonate, aqueous sodium hydrogen sulfite and aqueous saturated sodium chloride, then dried over anhydrous sodium sulfate. After concentration, the concentrate was purified on silica gel column chromatography to obtain 4-benzyloxy-2-methylsulfonyl-6-(trifluoromethyl)pyrimidine (Compound II-22).

Yield: 3.0 g. Melting point: 115°–118° C.

Reference Synthesis Example 3

Synthesis of 4-benzyloxy-6-bromo-2-(methylsulfonyl)pyrimidine (Compound II-23)

(1) Synthesis of 4-benzyloxy-6-bromo-2-(methylthio)pyrimidine

Benzyl alcohol (0.86 g, 0.00794×1.0 mol) was dissolved in tetrahydrofuran, and then sodium hydride (0.32 g (60% in mineral oil), 0.00794×1.0 mol) was added thereto to prepare an alkoxide.

4,6-Dibromo-2-(methylthio)pyrimidine (2.0 g, 0.00794 mol) was added thereto and the resulting solution was stirred for about 2 hours at room temperature.

The reaction solution was poured into water and extracted with ethyl acetate. The obtained organic phase was washed successively with aqueous saturated sodium hydrogen carbonate and aqueous saturated sodium chloride, and then dried over anhydrous sodium sulfate. After filtration and concentration, the concentrate was purified on silica gel column chromatography to obtain 4-benzyloxy-6-bromo-2-(methylthio)pyrimidine.

Yield: 2.05 g.

NMR data are shown in the Table 5 below (Compound VI-23).

(2) Synthesis of the Compound II-23

4-Benzyloxy-6-bromo-2-(methylthio)pyrimidine (1.92 g, 0.00616 mol) was dissolved in acetic acid, then 31% aqueous hydrogen peroxide (1.5 g, 0.00616×2.2 mol) was added thereto. The resulting solution was refluxed for about 3 hours.

The reaction solution was poured into iced water and extracted with ethyl acetate to separate an organic phase. The obtained organic phase was washed successively with aqueous sodium hydrogen sulfite and aqueous saturated sodium chloride, and then dried over anhydrous sodium sulfate. After filtration and concentration, the concentrate was purified on silica gel column chromatography to obtain 4-benzyloxy-6-bromo-2-(methylsulfonyl)pyrimidine (Compound II-23).

Yield: 2.1 g.

Reference Synthesis Example 4

Synthesis of 4-chloro-6-benzyloxy-2-(methylsulfonyl)pyrimidine (Compound II-24)

(1) Synthesis of 4-chloro-6-benzyloxy-2-(methylthio)pyrimidine

Benzyl alcohol (2.27 g, 0.021 mol) was dissolved in tetrahydrofuran, and then sodium hydride (0.106 g (60% in mineral oil), 0.021×1.2 mol) was added thereto to prepare an alkoxide.

4,6-Dichloro-2-(methylthio)pyrimidine (5.0 g, 0.021×1.2 mol) was added thereto and the resulting solution was stirred for about 2 hours at room temperature.

The reaction solution was poured into water and extracted with ethyl acetate. The obtained organic phase was washed with aqueous saturated sodium chloride, and then dried over anhydrous sodium sulfate. After filtration and concentration, the concentrate was purified on silica gel column chromatography to obtain 4-chloro-6-benzyloxy-2-(methylthio)pyrimidine.

Yield: 4.75 g.

NMR data are shown in the Table 5 below Compound VI-24).

(2) Synthesis of the Compound II-24

6-Benzyloxy-4-chloro-2-(methylthio)pyrimidine (4.0 g, 0.0150 mol) was dissolved in chloroform, and then meta-chloroperbenzoic acid (7.57 g, 0.0150×2.05 mol) was added thereto while cooling with iced water. The resulting solution was allowed to react for about 2 hours at room temperature.

The reaction solution was poured into aqueous saturated sodium hydrogen carbonate and shaken. The organic phase was separated, washed successively with aqueous sodium hydrogen sulfite and aqueous saturated sodium chloride, then dried over anhydrous sodium sulfate and concentrated. After this, the concentrate was purified on silica gel column chromatography to obtain 4-chloro-6-benzyloxy-2-(methylsulfonyl)pyrimidine (Compound II-24).

Yield: 4.56 g. Melting point: 74°–77° C.

Reference Synthesis Example 5

Synthesis of 4-benzyloxy-6-iodo-2-(methylsulfonyl)pyrimidine (Compound II-25)

(1) Synthesis of 4,6-diiodo-2-(methylthio)pyrimidine 4,6-Dichloro-2-(methylthio)pyrimidine (2.0 g, 0.0103 mol) was mixed with 57% hydroiodic acid (11.5 g, 0.0103× 5.0 mol), and then the resulting mixture was stirred for 5 hours at 70° C.

After allowed to cool, the reaction solution was poured into water and extracted with ether. The obtained organic phase was washed successively with aqueous sodium hydrogen sulfite, aqueous saturated sodium hydrogen carbonate and aqueous saturated sodium chloride, and then dried over anhydrous sodium sulfate. The solvent was distilled off to obtain 4,6-diiodo-2-(methylthio)pyrimidine.

Yield: 2.97 g.

(2) Synthesis of 4-benzyloxy-6-iodo-2-(methylthio)pyrimidine

Benzyl alcohol (0.71 g, 0.00661×1.0 mol) was dissolved in tetrahydrofuran, and then sodium hydride (0.24 g (60% in mineral oil), 0.00661×1.0 mol) was added thereto to prepare an alkoxide.

4,6-Diiodo-2-(methylthio)pyrimidine (2.5 g, 0.0661 mol) was added thereto and the resulting solution was stirred for about 3 hours.

The reaction solution was poured into water and extracted with ethyl acetate. The obtained organic phase was washed successively with aqueous saturated sodium hydrogen carbonate and aqueous saturated sodium chloride, and then dried over anhydrous sodium sulfate. After filtration and concentration, the concentrate was purified on silica gel column chromatography to obtain 4-benzyloxy-6-iodo-2-(methylthio)pyrimidine.

Yield: 1.59 g.

NMR data are shown in the Table 5 below (Compound VI-25).

(3) Synthesis of the Compound II-25

4-Benzyloxy-6-iodo-2-(methylthio)pyrimidine (1.30 g, 0.00362 mol) was dissolved in chloroform, and then meta-chloroperbenzoic acid (1.87 g, 0.00362 mol) was added thereto while cooling with iced water. The resulting solution was allowed to react for about 3 hours at room temperature.

The reaction solution was poured into aqueous saturated sodium hydrogen carbonate and shaken. The obtained organic phase was separated, washed successively with aqueous sodium hydrogen sulfite and aqueous saturated sodium chloride and then dried over anhydrous sodium sulfate. After filtration and concentration, the concentrate was purified on silica gel column chromatography to obtain 4-benzyloxy-6-iodo-2-(methylsulfonyl)pyrimidine (Compound II-25).

Yield: 0.90 g.

NMR data of the compounds synthesized in the above reference synthesis examples 1 to 5 as well as of those synthesized in a similar manner to these reference synthesis examples are shown in the Table 5.

TABLE 5

| No. | $^1$H-NMR (60 MHZ, CDCl$_3$, δ) |
|---|---|
| II-1 | 3.10(3H, s), 4.5–4.9(2H, m), 5.1–5.6(2H, m), 5.19(2H, s), 5.4–6.2 (1H, m), 7 1–7.6 (5H, m) |
| II-2 | 3.18(3H, s), 4.5–4.9(2H, m), 5.1–5.6(2H, m), 5.30(2H, s), 5.4–6.2(1H, m), 7.0–7.7(5H, m) |
| II-3 | 1.63(3H, s), 1.70(3H, s), 3.10(3H, s), 4.63(2H, d, J=7Hz), 5.1–5.5(1H, m), 5.20(2H, s), 7.1–7.8(6H, m) |
| II-4 | 2.49(3H, s), 3.26(3H, s), 5.43(2H, s), 6.68(1H, s), 7.33(5H, s) |
| II-5 | 2.17(3H, s), 3.20(3H, s), 5.20(2H, s), 6.8–7.6(5H, m) |
| II-6 | 3.10(3H, s), 3.86(3H, s), 5.15(2H, s), 7.1–7.6(5H, m) |
| II-7 | 2.25(3H, s), 3.15(3H, s), 3.89(3H, s), 5.13(2H, s), 6.9–7.7(5H, m) |
| II-11 | 2.27(3H, s), 3.22(3H, s), 3.85(3H, s), 5.10(2H, s), 6.9–7.5(5H, m) |
| II-12 | 3.22(3H, s)., 3.63(3H, s), 3.85(3H, s), 5.20(2H, s), 7.1–7.6(5H, m) |
| II-13 | 3.15(3H, s), 3.80(3H, s), 5.18(2H, s), 7.1–7.7(5H, m) |
| II-14 | 3.20(3H, s), 3.86(3H, s), 5.10(2H, s), 7.0–7.7(5H, m) |
| II-15 | 1.30 (3H, t, J=6.9Hz), 3.10 (3H, s) 4.25(2H, q, J=6.9Hz), 5.10(2H, s), 7.0–7.5(5H, m) |
| II-16 | 1.28(3H, t, J=6.9Hz), 3.15(3H, s), 4.30(2H, q, J=6.9Hz), 5.10(2H, s), 6.9–7.7(5H, m) |
| II-17 | 1.29(3H, t, J=6.9Hz), 3.25(3H, s), 4.33(2H, q, J=6.9Hz), 5.19(2H, s), 6.9–7.7(5H, m) |
| II-21 | 1.30(3H, t, J=6.9Hz), 3.15(3H, s), 4.28(2H, q, J=6.9Hz), 5.10(2H, s), 6.9–7.6(5H, m) |
| II-22 | 3.10(3H, s), 5.21(2H( s), 7.1–7.6(6H, m) |
| II-23 | 3.10(3H, s), 5.20(2H, s), 7.21(1H, s), 7.1–7.6(5H, m) |
| II-24 | 3.26(3H, s), 5.46(2H, s), 6.87(1H, s), 7.34(5H, s) |
| II-25 | 3.i1(3H, s), 5.10(2H, s), 7.0–7.8(6H, m) |
| VI-4 | 2.33(3H, s), 2.51(3H, s), 5.36(2H, s), 6.22(1H, s), 7.32(5H, s) |
| VI-23 | 3.10(3H, s), 5.20(2H, s), 7.21(1H, s), 7.1–7.6(5H, m) |
| VI-24 | 2.47(3H, s), 5.31(2H, s), 6.33(1H, s), 7.28(5H, s) |
| VI-25 | 3.11(3H, s), 5.10(2H, s), 7.0–7.8(6H, m) |

Reference Synthesis Example 6

Synthesis of 4-chloro-6-methylthio-2-[3-(trifluoromethyl)phenoxy]pyrimidine (an intermediate of the Compound I-32

4,6-Dichloro-2-[3-(trifluoromethyl)phenoxy]pyrimidine (1.82 g, 0.0059 mol) was dissolved in dimethylformamide, and then sodium thiomethoxide solution (2.75 g (15% aqueous solution), 0.0059×1.0 mol) was added dropwise thereto at room temperature.

After allowed to react for 2 hours at room temperature, the reaction solution was poured into water and extracted with ethyl acetate. The obtained organic phase was washed successively with aqueous saturated sodium hydrogen carbonate and aqueous saturated sodium chloride, then dried over anhydrous sodium sulfate and thereafter concentrated.

The concentrate was purified on silica gel column chromatography to obtain 4-chloro-6-methylthio-2-[3-(trifluoromethyl)phenoxy]pyrimidine.

Yield: 1.6 g.

Formulation examples and test examples will hereinafter be described. Kinds of carriers (diluents) and additives to be used, as well as mixing ratios thereof and the active ingredient content therein may be modified in a broad range.

In each of the formulation examples, the term "parts" denotes "parts by weight".

Formulation example 1

(wettable powder)

Compound I-1 50 parts

Lignin sulfonate 5 parts

Alkyl sulfonate 3 parts

Diatomaceous earth 42 parts

The above ingredients were mixed together and ground finely to form a wettable powder. The wettable powder may be applied after diluted with water.

Formulation example 2

(emulsifiable concentrate)

Compound (I-11) 25 parts

Xylene 65 parts

Polyoxyethylene alkylaryl ether 10 parts

The above ingredients were homogeneously mixed to form an emulsifiable concentrate. The emulsifiable concentrate may be applied after diluted with water.

Formulation example 3

(granules)

Compound (I-32) 8 parts

Bentonite 40 parts

Clay 45 parts

Lignin sulfonate 7 parts

The above ingredients were homogeneously mixed, blended with water and processed into a granular form by means of an extrusion granulator to give granules.

Test example 1

(Weed control test by foliage treatment)

A wettable powder of each test compound prepared as described in the Formulation example 1 was diluted with water to prepare a solution of the predetermined concentration. The herbicidal solution was applied at an application rate of 100 1/10 a (active ingredient rate: 500 g/10 a) onto the foliage of each plant grown to the 1 to 2 leaf stage. The tested plants were pot cultivated redroot pigweed (*Amaranthus retroflexus*), common blackjack (*Bidens pilosa*), wild mustard (*Sinapis arvensis*), common chickweed (*Stellaria media*), sicklepod (*Cassia obtusifolia*), black nightshade (*Solanum nigrum*), velvetleaf (*Abutilon theophrasti*), field bindweed (*Convolvulus arvensis*), wild chamomile (*Matricaria chamomilla*), cleavers (*Galium aparine*), ivyleaf speedwell (*Veronica hederaefolia*), green foxtail (*Setaria viridis*), barnyard grass (*Echinochloa frumentaceum*), wild oat (*Avena fatua*) and henry crabgrass (*Digitaria adscendens*).

On the 14th day after the application, weed control effects were evaluated by the following criterion.

Evaluation rating: 0 (no activity) to 5 (complete death)

The results are summarized in the Table 6(1/2 to 2/2).

TABLE 6

| No. | g/10 a | AR | BP | SA | SM | CO | SN | AT | CA |
|---|---|---|---|---|---|---|---|---|---|
| I-1 | 500 | 5 | 5 | 4.5 | 4 | 4 | 5 | 4.5 | 5 |
| I-2 | 500 | 0 | 3 | 1 | 3 | 0 | 4 | 1 | 1 |
| I-3 | 500 | 3 | 4 | 2.5 | 3 | 2 | 2 | 5 | 1 |
| I-4 | 500 | 1.5 | 1.5 | 2 | 3.5 | 2.5 | 4 | 0 | 0 |
| I-5 | 500 | 4.9 | 0 | 4.5 | 3 | 3 | 3 | 2 | 3 |
| I-6 | 500 | 3 | 2.5 | 3.5 | 4 | 2 | 3 | 3 | 2 |
| I-7 | 500 | 2 | 1.5 | 2 | 1.5 | 4 | 4.5 | 1.5 | 0.5 |
| I-11 | 500 | 4.5 | 4.5 | 5 | 5 | 4 | 5 | 5 | 4 |
| I-12 | 500 | 4.8 | 0 | 5 | 3.5 | 3.5 | 5 | 4 | 3.5 |
| I-13 | 500 | 3 | 2 | 4 | 4 | 4 | 3 | 3 | 2 |
| I-14 | 500 | 1 | 2.5 | 2 | 3.5 | 2.5 | 2.5 | 3 | 3 |
| I-15 | 500 | 2 | 3.5 | 4.5 | 3 | 3.5 | 3.5 | 4 | 4 |
| I-16 | 500 | 2 | 4 | 3.5 | 4 | 2 | 5 | 2 | 4 |
| I-17 | 500 | 4 | 0 | 4.5 | 2 | 3.7 | 4.9 | 4 | 4 |
| I-21 | 500 | 3.5 | 2.5 | 5 | 3 | 3 | 4.9 | 4 | 2 |
| I-22 | 500 | 4 | 0 | 4 | 4 | 3.5 | 4.9 | 1.5 | 0 |
| I-23 | 500 | 1 | 0 | 4 | 3 | 2.5 | 4.9 | 2 | 0 |
| I-24 | 500 | 2.5 | 0 | 3 | 2 | 2.5 | 4 | 4 | 1 |
| I-25 | 500 | 4 | 1.5 | 3 | 0 | 1.5 | 4 | 0 | 0 |
| I-26 | 500 | 3 | 0 | 4.5 | 2 | 3.5 | 4.5 | 4 | 2 |
| I-27 | 500 | 4.8 | 0 | 4.9 | 3 | 3 | 4.5 | 4 | 2 |
| I-31 | 500 | 2.5 | 1 | 4.5 | 3.5 | 4 | 4.5 | 3.5 | 3 |
| I-32 | 500 | 3.5 | 3 | 4.5 | 3 | 4 | 5 | 4.5 | 5 |
| I-33 | 500 | 3.5 | 3 | 5 | 4 | 4.5 | 5 | 4 | 3.5 |
| I-34 | 500 | 3 | 1.5 | 4 | 2 | 4 | 4.8 | 2 | 2.5 |
| I-35 | 500 | 4 | 2.7 | 4.5 | 2.5 | 3.5 | 4.5 | 3 | 1 |
| I-36 | 500 | 3.5 | 5 | 4.5 | 2.5 | 5 | 4.9 | 5 | 3 |
| I-37 | 500 | 4 | 0 | 4 | 1.5 | 3 | 3.5 | 2 | 2.5 |
| I-41 | 500 | 4 | 0 | 4.9 | 2 | 2 | 5 | 4 | 4.5 |
| I-42 | 500 | 3.5 | 1 | 5 | 3 | 4 | 5 | 3 | 3 |
| I-43 | 500 | 4.5 | 2.5 | 5 | 4 | 2 | 5 | 4.7 | 0 |
| I-44 | 500 | 4 | 4 | 5 | 5 | 4 | 3 | 3.5 | 4 |
| I-45 | 500 | 3.5 | 0 | 4.5 | 4 | 2 | 5 | 2.5 | 3 |
| I-46 | 500 | 4 | 0 | 5 | 2 | 3 | 5 | 4 | 2.5 |
| I-47 | 500 | 1 | 0 | 4.5 | 5 | 2.5 | 5 | 3 | 1 |
| I-51 | 500 | 3.5 | 1 | 0 | 2 | 3.5 | 5 | 3 | 3 |
| I-52 | 500 | 4.5 | 0 | 5 | 2 | 3 | 5 | 3 | 1.5 |
| I-53 | 500 | 4 | 4 | 3.5 | 4.5 | 2.5 | 0 | 2 | 2 |
| I-54 | 500 | 4 | 4.5 | 5 | 5 | 3 | 3 | 5 | 4 |
| I-55 | 500 | 4 | 4 | 4.5 | 5 | 3.5 | 5 | 4 | 3.5 |
| I-56 | 500 | 4.8 | 0 | 5 | 3.5 | 3.5 | 5 | 4 | 3.5 |

AR: *Amaranthus retroflexus*; BP: *Bidens pilosa*; SA: *Sinapis arvensis*; SM: *Stellaria media*; CO: *Cassia obtusifolia*; SN: *Solanum nigrum*; AT: *Abutilon theophrasti*; and CA: *Convolvulus arvensis*.

TABLE 6

| No. | g/10 a | MC | GA | VH | SV | EF | AF | DA |
|---|---|---|---|---|---|---|---|---|
| I-1 | 500 | 4.5 | 5 | 4 | 4.5 | 4.5 | 4 | 5 |
| I-2 | 500 | 2 | 3 | 2 | 0.5 | 0.5 | 0.5 | 1 |
| I-3 | 500 | 2.5 | 4 | 2 | 1.5 | 2 | 1 | 1 |
| I-4 | 500 | 1 | 1.5 | 2 | 0 | 0 | 0 | 0 |
| I-5 | 500 | 0 | 3.5 | 1.5 | 3.5 | 0 | 0 | 0 |
| I-6 | 500 | 2 | 4 | 4 | 3 | 4 | 2 | 3.5 |
| I-7 | 500 | 0 | 2 | 3 | 0.5 | 0 | 0 | 1 |
| I-11 | 500 | 4 | 5 | 5 | 5 | 4 | 4 | 5 |
| I-12 | 500 | 0 | 3.5 | 4.9 | 1.5 | 0.5 | 0 | 1.5 |
| I-13 | 500 | 4.5 | 4 | 3 | 3 | 4 | 3 | 3 |
| I-14 | 500 | 1 | 3 | 1 | 1.5 | 1 | 0.5 | 2 |
| I-15 | 500 | 2 | 4 | 2 | 2.5 | 2 | 1.5 | 3 |
| I-16 | 500 | 1.5 | 4.5 | 2 | 3 | 1.5 | 1.5 | 2 |
| I-17 | 500 | 0 | 4.8 | 2.5 | 2.5 | 1 | 2.5 | 0.5 |
| I-21 | 500 | 1 | 3.5 | 2.5 | 0.5 | 1.5 | 1.5 | 0.5 |
| I-22 | 500 | 0 | 4 | 4 | 0 | 0.5 | 0 | 0.5 |
| I-23 | 500 | 0 | 3.5 | 4 | 1.5 | 0.5 | 0 | 0.5 |
| I-24 | 500 | 0 | 2.5 | 2 | 0 | 0.5 | 0 | 1 |
| I-25 | 500 | 0 | 2 | 2.5 | 1.5 | 0 | 0 | 0.5 |
| I-26 | 500 | 1 | 3.5 | 1 | 0 | 0 | 0 | 0 |
| I-27 | 500 | 0 | 3.5 | 3 | 2 | 0 | 0 | 0 |
| I-31 | 500 | 1.5 | 4 | 4 | 0.5 | 0.5 | 0.5 | 0.5 |
| I-32 | 500 | 4 | 5 | 4.5 | 5 | 5 | 5 | 5 |
| I-33 | 500 | 4 | 3 | 3 | 4.5 | 5 | 3.5 | 5 |

TABLE 6-continued

| No. | g/10 a | MC | GA | VH | SV | EF | AF | DA |
|---|---|---|---|---|---|---|---|---|
| I-34 | 500 | 0 | 3.5 | 4.8 | 1.5 | 0.5 | 0 | 1.5 |
| I-35 | 500 | 0 | 1.5 | 0 | 0 | 1.5 | 0 | 0 |
| I-36 | 500 | 4.5 | 5 | 5 | 0.5 | 0 | 0 | 0 |
| I-37 | 500 | 0 | 2.5 | 1 | 0 | 0 | 0 | 1.5 |
| I-41 | 500 | 0 | 4 | 4.9 | 0 | 0 | 0 | 0.5 |
| I-42 | 500 | 0 | 2 | 2 | 2 | 0.1 | 0 | 0.1 |
| I-43 | 500 | 1 | 5 | 5 | 2 | 1.5 | 2 | 0.5 |
| I-44 | 500 | 4 | 4 | 4 | 4 | 3 | 3 | 4 |
| I-45 | 500 | 0 | 3.5 | 2 | 2 | 0 | 0 | 0 |
| I-46 | 500 | 2 | 3 | 1.5 | 3 | 0.5 | 0 | 0.5 |
| I-47 | 500 | 0 | 2 | 5 | 0 | 0 | 0 | 0.5 |
| I-51 | 500 | 0 | 3.5 | 3.5 | 1.5 | 0.1 | 0 | 2 |
| I-52 | 500 | 0 | 3 | 1.5 | 2 | 0 | 0 | 2 |
| I-53 | 500 | 0 | 1 | 4 | 3 | 4 | 2 | 4 |
| I-54 | 500 | 3 | 4 | 4 | 4 | 4 | 4 | 3.5 |
| I-55 | 500 | 4 | 4 | 5 | 5 | 4 | 4 | 4 |
| I-56 | 500 | 0 | 3.5 | 4.9 | 1.5 | 0.5 | 0 | 1.5 |

MC: *Matricria chamomilla*; GA: *Galium aparine*; VH: *Veronica hederaefolia*; SV: *Setaria viridis*; EF: *Echinochloa frumentaceum*; AF: *Avena fatua*; and DA: *Digitaria adscendens*.

Test example 2

(Seed germination test)

In each of 9 cm-diameter Petri dishes having the bottom covered with double sheets of filter paper, 6 ml of aqueous suspension of a test compound (containing 50 ppm of active ingredient) was poured and ten seeds of each plant were placed. The tested plants were green foxtail (*Setaria viridis*), barnyard grass (*Echinochloa oryzicola*), rice flatsedge (*Cyperus iria*) and rice (*Oryza sativa*).

The seeds was allowed to germinate in a constant-temperature chamber at 28° C., and on the 14th day after the sowing, the inhibition of germination and the retarding of growth were visually observed and evaluated by the following criterion.

Evaluation rating: 0 (no activity) to 5 (inhibition of germination or death after germination).

The results are summarized in Table 7.

TABLE 7

| No. | ppm | SV | EO | CI | Rice |
|---|---|---|---|---|---|
| I-1 | 50 | 4.9 | 4 | 4.5 | 3.5 |
| I-3 | 50 | 2.5 | 3 | 3 | 2 |
| I-4 | 50 | 0 | 0 | 0 | 0 |
| I-5 | 50 | 0 | 0 | 0 | 0 |
| I-6 | 50 | 2 | 1 | 2 | 1 |
| I-7 | 50 | 3.5 | 1 | 1 | 1 |
| I-11 | 50 | 4.5 | 4.5 | 4.9 | 3 |
| I-12 | 50 | 1 | 0.5 | 1 | 0.5 |
| I-13 | 50 | 2 | 3 | 1 | 1 |
| I-15 | 50 | 3.5 | 3.5 | 4 | 3 |
| I-16 | 50 | 2.5 | 4 | 4 | 2 |
| I-17 | 50 | 4 | 0 | 1 | 0.5 |
| I-21 | 50 | 3 | 2 | 3 | 1 |
| I-22 | 50 | 1.5 | 1 | 1.5 | 1 |
| I-23 | 50 | 2.5 | 1.5 | 0 | 0 |
| I-24 | 50 | 3 | 4 | 4 | 2 |
| I-25 | 50 | 0 | 0 | 0 | 0 |
| I-26 | 50 | 3 | 1 | 1 | 1 |
| I-27 | 50 | 2 | 0.5 | 1 | 0.5 |
| I-31 | 50 | 2 | 1.5 | 2 | 1 |
| I-32 | 50 | 4.5 | 5 | 4.5 | 4.5 |
| I-33 | 50 | 4 | 0 | 1 | 4.5 |
| I-34 | 50 | 4 | 1 | 1 | 1 |
| I-35 | 50 | 5 | 1.5 | 0 | 1 |
| I-36 | 50 | 3.3 | 4.5 | 4 | 3.5 |
| I-37 | 50 | 4 | 2 | 1.5 | 1 |

TABLE 7-continued

| No. | ppm | SV | EO | CI | Rice |
|---|---|---|---|---|---|
| I-41 | 50 | 4 | 0 | 1 | 0.5 |
| I-42 | 50 | 2 | 1 | 2 | 0 |
| I-43 | 50 | 3 | 3.5 | 4 | 0 |
| I-44 | 50 | 3.5 | 3.5 | 4 | 2.5 |
| I-45 | 50 | 3 | 1 | 1 | 1 |
| I-46 | 50 | 2 | 2 | 3.5 | 0.5 |
| I-47 | 50 | 3 | 0 | 1 | 0 |
| I-51 | 50 | 3 | 3 | 2.5 | 1 |
| I-52 | 50 | 1 | 2 | 1.5 | 1.5 |
| I-54 | 50 | 4.5 | 4.5 | 4.9 | 4.5 |
| I-55 | 50 | 4 | 4.5 | 4.5 | 3 |
| I-56 | 50 | 1 | 0.5 | 1 | 0.5 |

SV: *Setaria viridis*; EO: *Echinochloa oryzicola*; CI: *Cyperus iria*; and Rice: *Oryza sativa* (cultivar SASANISHIKI).

What is claimed is:

1. A benzyloxypyrimidine derivative of the formula (I):

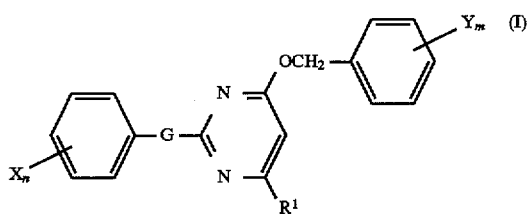

wherein $R^1$ represents hydrogen, a halogen, $C_1$–$C_4$ alkyl, $C_1$–$C_4$ haloalkyl, $C_1$–$C_4$ alkoxy, $C_1$–$C_4$ haloalkoxy, $C_3$–$C_5$ alkenyloxy, $C_1$–$C_4$ alkylthio, or cyano;

each X, which may be identical or different if n is greater than 1, represents a halogen, $C_1$–$C_4$ alkyl, $C_1$–$C_4$ haloalkyl, $C_1$–$C_4$ alkoxy, $C_1$–$C_4$ haloalkoxy, or $C_1$–$C_4$ haloalkylthio;

each Y, which may be identical or different if m is greater than 1, represents a halogen, $C_1$–$C_4$ alkyl, $C_1$–$C_4$ haloalkyl, $C_1$–$C_4$ alkoxy, or $C_1$–$C_4$ haloalkoxy;

G represents O or S; and n and m each independently represent an integer of 0 to 5.

2. A benzyloxypyrimidine derivative according to claim 1, wherein $R^1$ represents hydrogen, a halogen, methyl, methoxy, ethoxy, methylthio, ethylthio, or cyano.

3. A benzyloxypyrimidine derivative according to claim 1, wherein n is 0 or X represents a halogen, trifluoromethyl, 2,2,2-trifluoroethoxy, or 2,2,3,3,3-pentafluoropropoxy.

4. A benzyloxypyrimidine derivative according to claim 1, wherein m is 0 or Y represents a halogen, methyl, methoxy, or trifluoromethyl.

5. A herbicidal composition comprising a herbicidally effective amount of a benzyloxypyrimidine derivative of the formula (I):

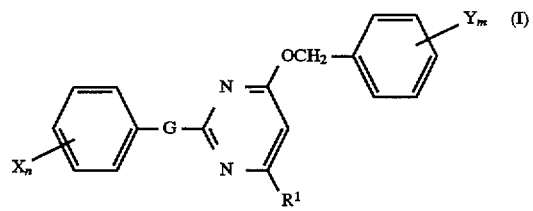

wherein $R^1$, X, Y, G, m, and n are as defined in claim 1, and an adjuvant.

6. A herbicidal composition according to claim 5, wherein $R^1$ represents hydrogen, a halogen, methyl, methoxy, ethoxy, methylthio, ethylthio, or cyano.

7. A herbicidal composition according to claim 5, wherein n is 0 or X represents a halogen, trifluoromethyl, 2,2,2-trifluoroethoxy, or 2,2,3,3,3-pentafluoropropoxy.

8. A herbicidal composition according to claim 5, wherein m is 0 or Y represents a halogen, methyl, methoxy, or trifluoromethyl.

* * * * *